United States Patent [19]

Gilpin et al.

[11] 4,402,877

[45] Sep. 6, 1983

[54] ADSORPTION AND RECOVERY OF RIFAMYCIN B AND RIFAMYCIN S USING BASIC ION EXCHANGE RESINS

[75] Inventors: Jo Ann Gilpin; Patrick J. Oriel; Roger A. Briggs, all of Midland, Mich.

[73] Assignee: The Dow Chemical Company, Midland, Mich.

[21] Appl. No.: 406,659

[22] Filed: Aug. 9, 1982

[51] Int. Cl.[3] .................. C07D 491/18; C07D 491/08

[52] U.S. Cl. .................................... 260/239.3 P

[58] Field of Search .......................... 260/239.3 P

[56] References Cited

U.S. PATENT DOCUMENTS

| | | | |
|---|---|---|---|
| 3,000,792 | 9/1961 | Denkewalter et al. | 195/80 |
| 3,122,565 | 2/1964 | Kijima et al. | 260/345.6 |
| 4,193,919 | 3/1980 | Briggs et al. | 260/239.3 P |

*Primary Examiner*—Robert T. Bond

*Attorney, Agent, or Firm*—Edward P. Gray; R. G. Brookens

[57] ABSTRACT

The use of basic ion exchange resins to adsorb rifamycin B or rifamycin S from dilute solutions containing rifamycin B or rifamycin S is disclosed. The rifamycin B or rifamycin S may be recovered from the resin by desorption with a suitable desorbing solvent system.

12 Claims, No Drawings

ADSORPTION AND RECOVERY OF RIFAMYCIN B AND RIFAMYCIN S USING BASIC ION EXCHANGE RESINS

BACKGROUND OF THE INVENTION

The antibiotic rifamycin S is a physiologically active derivative of the microbial fermentation product rifamycin B. Traditional methods of producing rifamycin S from rifamycin B require a complex, multi-step process. For example, rifamycin B can be oxidized by hydrogen peroxide or ammonium persulfate to the intermediate compound rifamycin O, subsequent acid hydrolysis of which yields rifamycin S. See T. Korzybski et al., *Antibiotics,* Volume I, pp. 250–267 (Pergamon Press, 1967).

Conventional solvent extraction techniques used for the recovery of these rifamycin derivatives require the use of large volumes of solvent and/or repetitive extractions. In addition, by-products are often extracted and concentration steps are usually required. More efficient recovery of the rifamycin derivatives at various stages in the fermentation process could lead to improved yields and/or process simplification.

Ion exchange resins have been used in the purification and recovery of certain antibiotics and other biologically active materials. For example, streptomycin has been adsorbed from a liquid culture by weakly acidic ion exchangers. J. Buchi, *J. Pharm. Pharmacol.,* 8, 379 (1956). Strong base resins have proven useful for work with phenolic compounds, for example, the recovery of the antibiotic novobiocin from a fermentation broth, U.S. Pat. No. 3,000,796 (1961); and for concentration of tocopherol, U.S. Pat. No. 3,122,565 (1964).

However, rifamycin derivatives are more difficult to work with than other biologically active materials because rifamycin derivatives are readily decomposed under basic conditions as well as under anhydrous acidic conditions. Therefore, the conditions used and the methods employed for the recovery of the rifamycin derivatives are important.

SUMMARY OF THE INVENTION

The present invention is directed to a process for separating rifamycin (i.e., rifamycin B or rifamycin S) from a solution containing from about 0.0001 percent to about 10 percent weight/volume (w/v) rifamycin by sequentially contacting the solution with a macroreticular base ion exchange resin under conditions sufficient to adsorb at least a portion of the rifamycin to the resin without appreciable decomposition of the rifamycin, and recovering the rifamycin adsorbed onto the resin by contacting said resin with a desorbing solvent system under conditions wherein the rifamycin is desorbed without appreciable decomposition.

As used herein, the term "appreciable decomposition" refers to decomposition to an extent wherein the antibiotic rifamycin is unable to exhibit physiologically beneficial effects upon a selected host.

As used herein, the term "rifamycin" refers to rifamycin B or rifamycin S unless otherwise specifically referred to.

A solution containing from about 0.0001 percent to about 10 percent w/v rifamycin can represent aqueous, organic, or aqueous/organic solutions in which rifamycin has the requisite solubility and is not subject to appreciable decomposition. Such solutions are discussed in greater detail, infra.

Strongly or weakly basic macroreticular anion exchange resins may be used in the method of this invention. Such resins must have the capacity of reversibly adsorbing rifamycin B or rifamycin S under the conditions described herein. Conversely, strong or weakly acidic cationic exchange resins are unsuitable for the methods of the present invention.

The present invention is particularly useful since it provides a means for removing rifamycin from a solution without the need to evaporate and/or organic solvent extract the rifamycin containing solution.

DETAILED DESCRIPTION OF THE INVENTION

Macroreticular resins of the type described herein adsorb rifamycin B or rifamycin S when said resin is contacted with a solution containing rifamycin. In carrying out the process of the present invention, the solution containing the rifamycin is contacted with a strong or weak base macroreticular anion exchange resin by, for example, mixing the solution and the resin together in a container as in a batch process or by passing a stream of the solution through a bed of resin in a continuous process as in a column adsorption. These processes for contacting the resin and the solution containing the rifamycin are well known to one skilled in the art. One skilled in the art will appreciate that it is not possible to give optimal process conditions for all of the variations of the present invention described herein, particularly when a column charged with a macroreticular resin is used. The exact conditions required for optimal performance is dependent upon the macroreticular resin used, the concentration of the rifamycin in the solution, the nature of the solution, the method used to contact the resin with the rifamycin-containing solution and other variables.

Macroreticular anion exchange resins suitable for the practice of the present invention generally, though not necessarily, have a styrene-divinylbenzene copolymer lattice. Such resins may be prepared by known procedures (see, for example, U.S. Pat. Nos. 3,549,562 and 3,637,535 which are incorporated herein by reference) or are commercially available.

Examples of commercially available strong base ion exchange resins which are operable in the practice of the present invention include, but are not limited to, Dowex MSA-1 ® (The Dow Chemical Co.) and Amberlite A-21 ® (Rohm and Haas). Examples of commercially available weak base ion exchange resins which are operable in the practice of the present invention include, but are not limited to, Dowex MWA-1 ® (The Dow Chemical Co.), Diaion WA-21 ® (Mitsubishi) and Duolite A-7 ® (Diamond Shamrock).

Other resins operable in the method of the present invention which are not commercially available include, but are not limited to resins having a styrene-divinylbenzene copolymer lattice with about 4 to about 12 percent cross-linking using about 30 to about 55 percent inert diluent and having, for example, a dimethylamine ion exchange functionality. Of these resins, one having 6 percent cross-linking using 49 percent inert diluent and having a dimethylamine ion exchange functionality is preferred and is hereinafter referred to as "6/49 DMA."

Resins found unsuitable in the practice of the present invention are the acid cation exchange resins, commercial examples of which include Dowex MSC-1 ® (The Dow Chemical Co.), Amberlite IRC-84® (Rohm and Haas) and Amberlite IRC-50® (Rohm and Haas).

In a typical batch adsorption method, the basic macroreticular resins are conditioned with solvent or an appropriate buffer prior to use. Batch adsorptions from aqueous solutions (including fermentation filtrates) use wet macroreticular resins conditioned in a solvent system which is the same as that in which the batch adsorption is to take place, except that the conditioning solution contains no rifamycin. Batch adsorptions from organic solvents are carried out with macroreticular resins which had been conditioned with the same organic solvent and, where resin stability allowed, vacuum dried overnight (60° C., 28 mm Hg) and then swelled with the organic solvent.

The batch adsorption may be demonstrated by suspending from about 0.5 to about 1.0 gram (g) of the macroreticular resin in from about 7 to about 25 milliliters (ml) of the rifamycin solution in a stoppered flask at 25° C. The equilibrium adsorption of the particular rifamycin compound is determined after 24 hours by comparing the absorption spectrum of the liquid phase with that of the original rifamycin solution (in some cases as little as six hours is required for equilibrium adsorption). The quantity of adsorbed rifamycin per gram of macroreticular resin is calculated by measuring the rifamycin concentration in the test solution prior to, and after contact with the macroreticular resin, and noting the difference.

Rifamycin B or rifamycin S can be desorbed from the particular basic macroreticular resin used for adsorption by contacting said resin with a suitable desorbing solvent system consisting of at least one organic solvent in which rifamycin B or S has the requisite solubility and containing a minor amount of a dilute aqueous acid such that the pH of the desorbing solvent system is from about pH 0 to about 7.

The organic solvents in which rifamycin B has good solubility include, but are not limited to, tetrahydrofuran, dioxane, acetonitrile, ethyl acetate, and lower alcohols of from about one to about four carbon atoms inclusive. Of the organic solvents in which rifamycin B has good solubility, tetrahydrofuran and methanol containing solvent systems are preferred.

Organic solvents in which rifamycin S has good solubility include, but are not limited to, chlorinated hydrocarbons (such as chloroform or methylene chloride), tetrahydrofuran, dioxane, ethyl acetate and lower alcohols of from about one to about four carbon atoms inclusive. Of the organic solvents in which rifamycin S has good solubility, chloroform/methanol and methylene chloride/methanol containing solvent systems are preferred.

Most organic or mineral acids can be used in the above-mentioned desorbing solvent systems. For example, organic acids such as acetic, benzoic, formic, malonic, oxalic or maleic acids or mineral acids, such as hydrochloric, phosphoric or sulfuric acids are suitable.

In general, when the rifamycin is adsorbed utilizing a batch adsorption procedure, rifamycin B or rifamycin S can be desorbed from the resin by mixing about 0.5 to about 1.0 g of the macroreticular resin containing the adsorbed rifamycin with about 7 to about 20 ml of the suitable desorbing solvent system for a period of time sufficient to achieve desorption. When the adsorption is accomplished utilizing a continuous process, such as a column charged with a macroreticular resin, desorption may be achieved by passing the suitable desorbing solvent system through the column at a flow rate of about 2 ml/cm$^2$ min. In either instance, the amount of desorbed rifamycin is determined from the visible absorption spectrum (300–500 mμ) of the soluble phase by comparison with a standard of known concentrations. To confirm the absence of rifamycin decomposition following desorption, conventional techniques such as thin layer chromatography may be employed.

As previously noted herein, solutions containing from about 0.0001 to about 10 percent of rifamycin B or rifamycin S are either aqueous, organic or aqueous/organic solutions. An aqueous solution is, for example, a fermentation filtrate or aqueous buffer system, such as phosphate or tris(hydroxymethyl)aminomethyl buffers, or calcium carbonate-carbon dioxide buffers or aqueous solutions adjusted by an acid or base to pH of about 1 to about 10. However, because rifamycins are pH sensitive, a pH of from about 5.5 to about 8 is preferred for adsorption.

Table 1, below, summarizes the adsorption of rifamycin B from various solutions containing rifamycin B by certain of the macroreticular resins described herein utilizing a batch adsorption technique (unless otherwise indicated). Representative examples of the adsorptions described in Table 1 are discussed in detail below.

TABLE 1

| Rifamycin B Solution | Effective Adsorption Resin | Percent of Available Rifamycin B Adsorbed Onto Resin | mg of Rifamycin B Adsorbed per gram of Resin[1] |
|---|---|---|---|
| 0.1% Rifamycin B in 0.1 M phosphate buffer (pH 7.4) | Dowex MWA-1 ® (The Dow Chemical Co.) | 96 | 14 |
| | Diaion WA-21 ® (Mitsubishi) | >99 | 15 |
| 0.5% Rifaymcin B in 0.1 M phosphate buffer (pH 7.3) | Duolite A-7 ® (Diamond Shamrock) | 42 | 42 |
| | Dowex MWA-1 ® (The Dow Chemical Co.) | 93 | 92 (dry resin) |
| | Dowex MSA-1 ® (The Dow Chemical Co.) | 85 | 84 (dry resin) |
| 0.5% Rifamycin B in tetrahydrofuran | Dowex MWA-1 ® (The Dow Chemical Co.) | 92 | 93 (dry resin) |
| 0.5% Rifamycin B in 0.1 M phosphate buffer (pH 7.2) | 6/49 DMA | 54 | 81 |
| 0.7% Rifamycin B in 0.1 M phosphate buffer (pH 7.4) | 6/49 DMA | 96 | 69 |
| | Diaion WA-21 ® (Mitsubishi) | 97 | 69 |
| 0.76% Rifamycin B in a fermentation filtrate (pH 7.4) | 6/49 DMA | 70[2] | 51 |

[1]Wet resin used unless otherwise indicated.
[2]Adsorption was achieved using a column adsorption technique. Percent adsorbed was at three resin bed volumes of influent.

Desorption of rifamycin B is accomplished by contacting the macroreticular resin containing adsorbed rifamycin B with a suitable desorbing solvent system as previously described. For example, a desorbing solvent system for rifamycin B containing of from about 80 to about 99 parts of methanol, from about 0.5 to about 20 parts water and less than 1 part mineral acid or less than 10 parts organic acid may be used. Preferably, the desorbing solvent system for rifamycin B will contain about 95 parts methanol, 5 parts water and less than 1 part mineral acid or less than 10 parts organic acid. Also preferred as a desorbing solvent system for rifamycin B is a system containing from about 85 to about 100 parts tetrahydrofuran and from about 0 to about 15 parts dilute, aqueous mineral acid. Especially preferred as a desorbing solvent system for rifamycin B is a system containing 90 parts tetrahydrofuran and 10 parts dilute, aqueous mineral acid.

Table 2, below, summarizes the adsorption of rifamycin S from various solutions containing rifamycin S by certain of the macroreticular resins described herein utilizing a batch adsorption technique. Representative examples of the adsorptions described in Table 2 are discussed in detail below.

TABLE 2

| Rifamycin S Solution | Effective Adsorption Resin | Percent of Available Rifamycin S Adsorbed Onto Resin | mg of Rifamycin S Adsorbed per gram of Resin[1] |
|---|---|---|---|
| 0.08% Rifamycin S in 0.1 M phosphate buffer (pH 7.2) | 6/49 DMA | 77 | 28 (wet resin) |
| 0.08% Rifamycin S in 0.1 M phosphate buffer (pH 7.3) | Dowex MSA-1 ® (The Dow Chemical Co.) | 25 | 10 |
| | Dowex MWA-1 ® (The Dow Chemical Co.) | 79 | 32 |
| | Duolite A-7 ® (Diamond Shamrock) | 14 | 6 |
| 0.1% Rifamycin S in chloroform | Dowex MWA-1 ® (The Dow Chemical Co.) | 79 | 13 |
| | 6/49 DMA | 76 | 11 |
| | Diaion WA-21 ® (Mitsubishi) | >98 | 15 |
| 0.1% Rifamycin S in chloroform/methanol/water (78/18/2) | 6/49 DMA | 55 | 11 |
| | Diaion WA-21 ® (Mitsubishi) | 91 | 18 |

[1]Dry resin used unless otherwise indicated.

Desorption of rifamycin S is accomplished by contacting the macroreticular resin containing the rifamycin S with a suitable desorbing solvent system as previously described. For example, a desorbing solvent system for rifamycin S containing greater than 80 parts chloroform, from about 5 to about 15 parts methanol, from about 0.5 to about 5 parts water and less than 1 part mineral acid or less than 20 parts organic acid may be used. Preferably, the desorbing solvent system for rifamycin S will contain about 80 to about 90 parts chloroform, about 10 parts methanol, less than 10 parts organic acid and from about 0.5 to about 3 parts water. Of the preferred desorbing solvent systems for rifamycin S, the system containing 84 parts chloroform, 9.5 parts methanol, 5.6 parts acetic acid and 0.9 parts water is especially preferred.

The following examples illustrate the recovery of rifamycin B or rifamycin S from solutions containing rifamycin B or rifamycin S. They are specific examples illustrating the invention and are not intended as a limitation thereon. The resins used in the following examples were conditioned prior to use as previously described.

EXAMPLE 1

A column containing the weak base ion exchange resin 6/49 DMA was prepared using a 1.8 ml fill volume of the resin to charge a column having a cross-sectional area of 0.21 square centimeters ($cm^2$). The column was contacted with a fermentation filtrate containing 0.76 percent rifamycin B (pH 7.4) at a flow rate through the column of 0.30 ml/minute (min) which gave a resin loading of 51 milligrams (mg) of rifamycin B per ml of resin. The rifamycin B was desorbed from the resin by passing a methanol/water (95/5) solution containing 1.0 N malonic acid through the column at a flow rate of 0.42 ml/min. Recovery of the rifamycin was nearly quantitative (subsequent thin layer chromatography indicated that an impurity present in the particular fermentation filtrate used had also been selectively adsorbed by the resin).

EXAMPLE 2

A small column (11.5 centimeters in height having a cross-sectional area of 0.21 $cm^2$) containing the weak base ion exchange resin Diaion WA-21 ® (Mitsubishi), a polyamine resin was prepared. The column was contacted with an aqueous 0.1 M phosphate buffer (pH 7.3) having a rifamycin B concentration of 1 mg/ml. The adsorption was carried out at 24° C. with a normalized liquid flow through the column of 1.09 ml/$cm^2$ min and a mean contact time of 4.0 minutes. Adsorption of rifamycin B by the resin was determined by following the absorption spectra of the column effluent. A resin loading of 27.6 mg of rifamycin B/ml of resin was obtained.

EXAMPLE 3

0.5 gram of dry Dowex MWA-1 ® (The Dow Chemical Company) resin was suspended in 10 ml of a rifamycin solution containing about 0.5 percent rifamycin B in a 0.1 M aqueous phosphate buffer (pH 7.3) at 25° C. The equilibrium adsorption was determined at 24 hours. The resin adsorbed 93 percent of the rifamycin B.

Desorption of the rifamycin B was effected by contacting the resin containing the adsorbed rifamycin B with 10 ml of a solution containing 9 ml of tetrahydrofuran and 1 ml dilute phosphoric acid for 10 minutes (the dilute phosphoric acid was composed of 4.0 ml of 85 percent $H_3PO_4$ diluted to 100 ml with $H_2O$). About 38 percent of the rifamycin B available on the resin was desorbed into the solvent system.

EXAMPLE 4

Using substantially the same materials and methods described in Example 3, 10 ml of a solution containing about 0.5 percent rifamycin B in tetrahydrofuran was contacted with Dowex MWA-1 ® (The Dow Chemical Company) resin. The resin adsorbed 92 percent of the rifamycin B. About 46 percent of the rifamycin B available on the resin was desorbed utilizing the same desorbing solvent system described in the previous example.

EXAMPLE 5

About 0.5 g of 6/49 DMA resin was conditioned as previously described herein. The resin was then mixed with about 7.5 ml of chloroform containing about 0.1 percent rifamycin S for 24 hours. The resin adsorbed about 76 percent of the rifamycin S.

Desorption was carried out by mixing the resin containing rifamycin S with 7.5 ml of a solvent system containing 84 parts chloroform, 9.5 parts methanol, 5.6 parts acetic acid and 0.9 parts water for about 1.5 hours. About 85 percent of the rifamycin S available on the resin was desorbed into the solvent system.

EXAMPLE 6

0.5 gram of Dowex MWA-1® (The Dow Chemical Company) resin was suspended in 25 ml of a rifamycin solution containing about 0.08 percent rifamycin S in a 0.1 M aqueous phosphate buffer (pH 7.3) at 25° C. The equilibrium adsorption was determined at 24 hours. The resin adsorbed 79 percent of the rifamycin S.

Desorption of the rifamycin S was achieved by contacting the resin containing the adsorbed rifamycin S with 10 ml of the desorbing solvent system described in Example 5 for about 4 hours. About 91 percent of the rifamycin S available on the resin was desorbed into the solvent system.

What is claimed is:

1. A process for separating rifamycin B or rifamycin S from a solution containing from about 0.0001 percent to about 10 percent weight/volume of rifamycin B or rifamycin S which comprises the sequential steps of:

(a) contacting said solution with a macroreticular resin under conditions at which at least a portion of the rifamycin B or rifamycin S available is adsorbed by the macroreticular resin without appreciable decomposition of the rifamycin B or rifamycin S, and (b) recovering the rifamycin B or rifamycin S by contacting the macroreticular resin containing the rifamycin B or rifamycin S with a desorbing solvent system under conditions at which the rifamycin B or rifamycin S is desorbed without appreciable decomposition of the rifamycin B or rifamycin S.

2. The process of claim 1 wherein the solution containing the rifamycin B or rifamycin S is an aqueous, organic or aqueous/organic solution.

3. The process of claim 1 wherein the macroreticular resin is a strong or weak base ion exchange resin.

4. The process of claim 3 wherein the strong base macroreticular ion exchange resin is selected from the group consisting of Dowex MSA-1® (The Dow Chemical Company) and Amberlite A-21® (Rohm and Haas).

5. The process of claim 3 wherein the weak base macroreticular ion exchange resin is selected from the group consisting of Dowex MWA-1® (The Dow Chemical Company), Diaion WA-21® (Mitsubishi), Duolite A-7® (Diamond Shamrock), and 6/49 DMA.

6. The process of claim 1 wherein the desorbing solvent system for rifamycin B contains from about 80 to about 99 parts methanol, from about 0.5 to about 20 parts water and less than 1 part mineral acid or less than 10 parts organic acid.

7. The process of claim 6 wherein the desorbing solvent system contains 95 parts methanol, 5 parts water and less than 1 part mineral acid or less than 10 parts organic acid.

8. The process of claim 1 wherein the desorbing solvent system for rifamycin B contains from about 85 to about 100 parts tetrahydrofuran and from about 0 to about 15 parts dilute, aqueous mineral acid.

9. The process of claim 8 wherein the desorbing solvent system contains 90 parts tetrahydrofuran and 10 parts dilute, aqueous mineral acid.

10. The process of claim 1 wherein the desorbing solvent system for rifamycin S contains greater than 80 parts chloroform, from about 5 to about 15 parts methanol, from about 0.5 to about 5 parts water and less than 1 part mineral acid or less than 20 parts organic acid.

11. The process of claim 10 wherein the desorbing solvent system contains from about 80 to about 90 parts chloroform, about 10 parts methanol, from about 0.5 to about 3 parts water, and less than 10 parts organic acid.

12. The process of claim 11 wherein the desorbing solvent system contains 84 parts chloroform, 9.5 parts methanol, 0.9 parts water and 5.6 parts acetic acid.

* * * * *